United States Patent [19]

Cooke

[11] Patent Number: 4,642,124
[45] Date of Patent: Feb. 10, 1987

[54] HIP PROSTHESIS

[75] Inventor: Francis W. Cooke, Clemson, S.C.

[73] Assignee: Clemson University, Clemson, S.C.

[21] Appl. No.: 619,496

[22] Filed: Jun. 11, 1984

[51] Int. Cl.$^4$ .............................................. A61F 2/32
[52] U.S. Cl. .................................................... 623/23
[58] Field of Search ......................... 3/1.9, 1.91, 1.911, 3/1.912, 1.913; 128/92 C, 92 CA, 92 B, 92 BC; 623/16, 17, 18, 19, 26, 21, 22, 23, 2

[56] References Cited

U.S. PATENT DOCUMENTS

| | | | |
|---|---|---|---|
| 2,785,673 | 3/1957 | Anderson | 623/22 |
| 3,863,273 | 2/1975 | Averill | 3/1.913 |
| 3,879,767 | 4/1975 | Stubstad | 623/18 |
| 3,893,196 | 7/1975 | Hochman | 3/1.913 |
| 3,938,198 | 2/1976 | Kahn | 623/23 |
| 4,012,796 | 3/1977 | Weisman | 3/1.913 |
| 4,068,324 | 1/1978 | Townley | 623/23 |
| 4,227,265 | 10/1980 | Frey | 623/22 |
| 4,280,233 | 7/1981 | Raab | 623/18 |
| 4,314,381 | 2/1982 | Koeneman | 128/92 CA |
| 4,404,672 | 9/1983 | Eftekhar | 623/22 |
| 4,454,612 | 6/1984 | McDaniel et al. | 128/92 CA |
| 4,523,587 | 6/1985 | Frey | 623/22 |

FOREIGN PATENT DOCUMENTS

| | | | |
|---|---|---|---|
| 0017743 | 10/1980 | Fed. Rep. of Germany | 623/22 |
| 2425237 | 1/1980 | France | 128/92 CA |
| 2475891 | 8/1981 | France | 623/22 |
| 1409053 | 10/1975 | United Kingdom | 3/1.913 |

OTHER PUBLICATIONS

"Durability of Femoral Implant Parts Intotal Hid Replacement: The Ultimate Test", Charles O. Bechtol, M.D., 1975.

37 The Bonding of Prostheses to Bone by Cement", John Charnley, 1964.
"Proximal Strain Distribution in the Loaded Femur", Harris, 1978.
"Proceedings and Reports of Universities, Colleges, Councils, and Associations" 1979.
"Implant Fixation", Miller, Krause, Krug, Kalaby, 1982.
"The Science of Better Fit".
"A – Radiological Study of Fractures of Acrylic Cement in Relation to the Stem of a Femoral Head Prosthesis", Weber, 1975.

Primary Examiner—Richard J. Apley
Assistant Examiner—David Isabella
Attorney, Agent, or Firm—Dority & Manning

[57] ABSTRACT

An improved hip prosthesis designed to simulate forces on a femur like those experienced by a normal, healthy femur. A ball is located atop the prosthesis at a proper anatomical angular relationship with a neck and collar therebelow. The prosthesis stem extends from the collar to a distal tip and includes a buttress section, a middle section and tip section. An inner surface of the buttress section is relieved and a compressible material is located thereat. The middle and tip sections of the stem are smooth, of common cross section, without any significant taper and the tip is adapted to avoid transmission of significant axial forces to the femur therebelow. When implanted with a luting agent, the majority of forces are axial compressive forces applied to the calcar and there is little or no wedging of the prosthesis in the medullary canal; little or no shear forces across the prosthesis - luting agent interface; and little or no axial stresses from the prosthesis tip distal to same.

7 Claims, 6 Drawing Figures

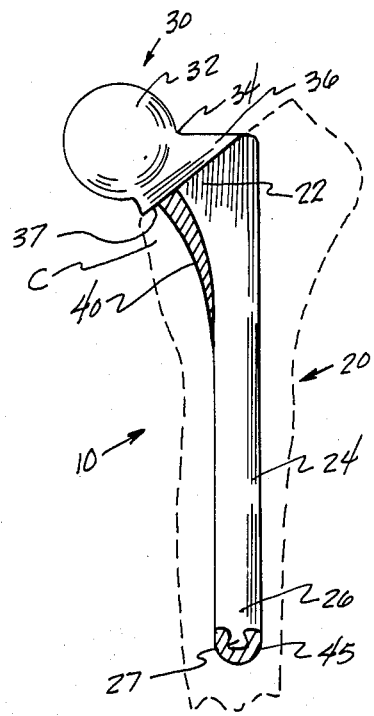
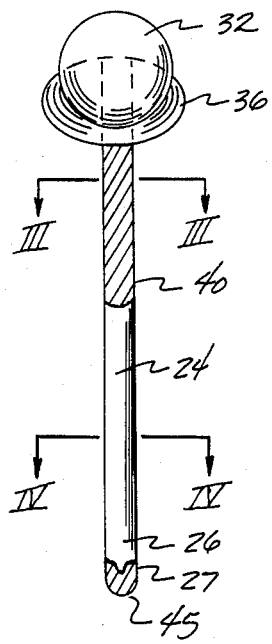
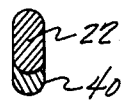
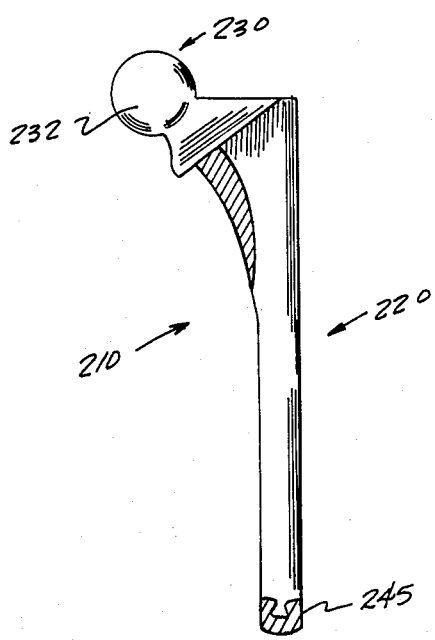
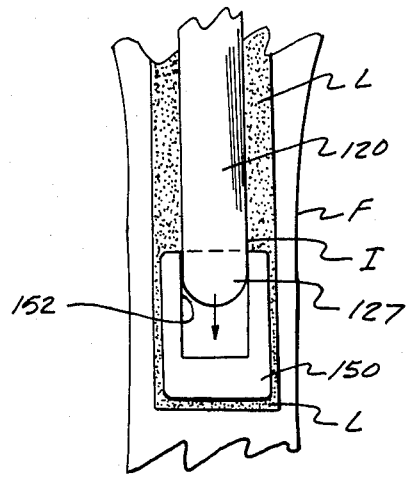

HIP PROSTHESIS

BACKGROUND OF THE INVENTION

The present invention relates to an improved hip prosthesis.

Prosthetic replacement of diseased and/or damaged hips, though not yet totally perfected, is a widely accepted surgical approach which has received a significant degree of success. In general, many years ago, surgeons began to surgically implant one piece hip prostheses having a stem and head where the head articulates within the natural acetabulum or an acetabular cup, while the stem of the prosthesis extends downwardly into the medullary canal. Initially, such was achieved by an elongated stem which was simply inserted directly into the marrow cavity. The distal tip of the prosthesis resided in soft marrow tissue and could move laterally from side to side. As the patient walked, the prosthesis was subject to toggling, whereby the prosthesis loosened within the femur, leading to resorption or other destruction of the supporting bone. Further attempts have since been made to create a prosthetic device that could be successfully implanted in a patient's hip without the subsequent loosening effect. In general, loosening of the prosthesis normally leads to a characteristic course of deterioration of the bone, resulting in serious loss of hip function and/or pain.

Under impingement fixation as mentioned above, the distal portion of the stem could move laterally to and fro when the patient walked. This movement approximated rotation about the connection between the stem and the head in the calcar region. After prosthesis failure, further surgery or patient inactivity resulted. In order to overcome the distal tip movement, loosening of the prosthesis and the consequential "windshield wiper effect", dental bone cement, which is in essence a chemical composition which polymerizes in situ within the medullary canal, was placed about the stem of the prosthesis within a slightly reamed medullary cavity to block the lateral movement of the stem within the medullary canal. Initially, only small amounts of bone cement were employed with realization of great improvement. Thereafter, surgeons further reamed the medullary canal and inserted greater amounts of bone cement according to the thesis that a greater bond, and thus more permanent fixation would result. While a more rigid initial fixation resulted, after prolonged periods of time, calcar bone resorption and fracture of the bone cement often occurred, leading to a recurrence of pathological processes, and perhaps replacement of the prosthesis.

Further, during polymerization of bone cement, generally a polymethylmethacrylate polymer, a significant exotherm is generated and less than total polymerization is achieved. Residual toxic monomeric substances thus remain in the medullary canal. Both the exotherm and the monomeric materials can produce adverse effects.

Still further, in order to approximate the normal anatomical shape to the femur, modern hip prostheses have conventionally included curved and tapered stems in order to facilitate insertion, while also avoiding the necessity of inordinate reaming of the femur. Such tapered shapes, in essence act as a wedge, such that subsequent to implantation, normal activity creates forces against the prosthesis which are transmitted via the tapered stem to the femur in undesirable directions in certain localized conditions. Particularly, with continued activity and some loosening of the prosthesis, loss of calcar bone results due to resorption. A loss of axial compressive force on the calcar is also believed to lead to resorption of the calcar bone, further compounding the loosening problem. The distal tip of the prosthesis stem engages a bolus of bone cement located thereneath, and a reduction of applied forces at the calcar results in an increase in axial compressive forces from the distal tip to the cement. Upon receipt of adequate force, the cement distal to the prosthesis tip fractures, permitting subsidence of the prosthesis and/or forcing of the polymerized bone cement further into the canal, again resulting in excessive loosening. Furthermore, the "wedging" resulting from tapered prostheses stems accounts for decreased axial compressive strains and increased tensile hoop stresses in the calcar. Also, at the level of the prosthesis tip, both axial compressive load and bending moments act on the femur, being transferred entirely to the bone at this level, and resulting in regions of increased strain.

The above noted altered strain patterns on the calcar is a major factor leading to remodeling of the bone and resorption of the calcar since the calcar bone is no longer required to support the entire joint load as with a normal, healthy femur. Particularly, a change in stress orientation from predominantly axial compression to predominantly circumferential tension creates stress across the grain of the bone as opposed to along the grain as provided by nature.

A number of factors have thus been proposed as possible contributory causation to prosthesis loosening, namely stress shielding of the calcar femorale; surgical impairment of blood supply in or around the implanted prosthesis; necrosis of bone tissue due to the exotherm produced during polymerization of bone cement; necrosis of bone tissue due to toxic substances released from the bone cement; relative movement at the bone cement interface during activity; and mechanical failure of the cement, particularly in the calcar region. Further and quite importantly, particulate matter produced from wear, bone erosion cement fracture and the like can develop after implantation, become entrapped within the reamed medullary canal, and provoke persistent local inflamation.

The hip prosthesis according to the present invention overcomes at least certain of the aforementioned problems by way of a unique prosthesis design which better approximates physiological axial compressive loading of the calcar while avoiding wedging and axial load transfer from the distal tip of the prosthesis stem to the femur. While the hip prosthesis of the present invention is implanted with the use of a luting agent such as bone cement, the instant prosthesis is manufactured to preclude load transfer to the luting agent by shear stresses acting across the prosthesis-luting agent interface or by direct impingement of the tip on the subjacent luting agent. Particularly, the design of the prosthesis according to the present invention permits continual contact between the prosthesis and the calcar bone to generate the approximate axial compressive stresses therein. The stem of the prosthesis is also provided with a generally uniform cross section such that only minimal wedging is experienced.

There is no known prior art that is believed to anticipate or suggest the hip prosthesis according to the present invention. Exemplary of the known prior art are U.S. Pat. Nos. 2,785,673; 3,879,767; 3,938,198; 4,012,796; 4,051,559; 4,068,324; 4,227,265; and 4,280,233.

SUMMARY OF THE PRESENT INVENTION

It is an object of the present invention to provide an improved hip prosthesis.

Another object of the present invention is to provide an improved hip prosthesis which subsequent to implantation, will create compressive stresses on the calcar bone that approach the stresses encountered by a healthy femur.

Another object of the present invention is to provide an improved hip prosthesis which subsequent to implantation will create hoop tensile stresses in the calcar bone that approach the stresses encountered by a healthy femur.

Yet another object of the present invention is to provide an improved hip prosthesis which, after implantation, creates only minimal wedging within the medullary canal accompanied by an appropriate application of forces generally experienced by the normal femur.

Still further, another object of the present invention is to provide an improved hip prosthesis which is less likely to cause resorption and remodeling of the surrounding bone structure, thus leading to a prolonged period of successful use.

Still another object of the present invention is to provide an improved hip prothesis which during use avoids the introduction of localized high tensile stresses in the luting agent utilized therewith, and avoids subsequent concentrations of stress due to loosening, bone resorption, and wedging.

Generally speaking, the improved hip prosthesis of the present invention comprises a medullary stem which includes a buttress section, a middle section and a distal tip section, said middle and distal tip sections having substantially uniform cross-sectional dimensions along at least a major portion of the length of same and presenting smooth, uninterrupted outer surfaces therearound, said buttress section increasing in dimension in a superior direction with respect to said middle section and having a compressible material associated therewith along an inferior surface of same; and a head secured to said stem at said buttress section and being angularly offset therefrom according to conventional anatomical criteria, said head including a ball section, a neck section distal to said ball section, and a collar distal to said neck section, said collar being juxtaposed to said buttress section of said stem and protruding radially outwardly therefrom, said distal tip section of said stem being adapted to preclude transmission of significant axial forces from said stem to bony structure distal to same.

More specifically, the prosthesis according to the present invention is basically of unitary construction insofar as the stem and head sections are concerned with the collar located juxtaposed the buttress section of the stem and being adapted for direct contact between a distal surface of same and the osteotomized surface of the femoral calcar. The stem in general is provided with straight, parallel outer edges to be received within the medullary canal of the femur, and having an enlarged buttress section along an inferior side of the prosthesis terminating at the collar to accommodate bending moments. The inferior surface of the buttress section is relieved from a point adjacent the collar downwardly to a point in the middle stem section where the cross section of the stem becomes constant. A compressible material is associated with the stem, located at the relieved area of the buttress and middle stem sections and is adequate in thickness to ensure persistent contact between the collar and the calcar bone, and to reduce wedging of the prosthesis within the femur.

With a major portion of the prosthesis stem having a generally uniform cross section and outer surfaces of same being continuous and absent any fenestrations, openings or the like, and in fact, being highly polished, when implanted in the femur, luting agent received thereabout secures the stem against lateral movement with no significant wedging, and without the transfer of any substantial shear forces across the stem-luting agent interface. In fact, polished surfaces of the stem may be coated with various lubricant type materials that further reduce the incidence of transfer of shear forces across the stem-luting agent interface. Additionally, the distal tip of the prosthesis stem is adapted to preclude the transmission of axial compressive forces from the prosthesis to the luting agent and or bone received about the distal tip. In a preferred arrangement, a compressible material is received about the distal tip or conversely the distal tip is located within a receiving element therefor that is implanted within the femur such that upon receipt of downward axial force, should the prosthesis be permitted to subside within the femur, the distal tip moves further within the receiving element without transmitting any substantial axial or compressive forces therebeyond.

BRIEF DESCRIPTION OF THE DRAWINGS

FIG. 1 is a side elevational view of a hip prosthesis according to the present invention having a ball section for receipt in the natural acetabulum.

FIG. 2 is an elevational view of the prosthesis as shown in FIG. 1 viewed from an inferior side of same.

FIG. 3 is a horizontal cross-sectional view of the prosthesis illustrated in FIG. 2 taken along a line III—III.

FIG. 4 is a horizontal cross-sectional view of the prosthesis shown in FIG. 2 taken along a line IV—IV.

FIG. 5 is a side elevational view of a further embodiment of a prosthesis according to the present invention illustrating a ball for receipt in an implanted acetabular cup.

FIG. 6 is a cross-sectional view of a distal tip portion of an implanted prosthesis according to the present invention illustrating a further embodiment of same.

DESCRIPTION OF THE PREFERRED EMBODIMENTS

Making reference to the Figures, preferred embodiments of the present invention will be described in detail. FIGS. 1–4 illustrate a preferred embodiment of the present invention in which a prosthesis generally indicated as 10 of unitary construction is illustrated. Prosthesis 10 includes a stem section generally 20 and a ball section generally 30 of unitary construction therewith and extending outwardly therefrom at a proper angular relationship according to the anatomical characteristics of the relationship between the femur and the hip joint. Stem section 20 basically includes a buttress section 22, a middle section 24 and a distal section 26. Ball section 30 includes a ball 32, a neck 34 located distal to ball 32, and a collar 36 that is juxtaposed to buttress section 22 and extends laterally outwardly therefrom. Collar 36 includes a shoulder or distal surface 37 along the underside of same that extends outwardly from stem 20 for engagement with the osteomotized surfaces of the calcar bone. An inferior side of buttress section 22 of stem 20 is relieved from a point adjacent distal shoulder surface 37 of collar 36 to medial section 24, and a compressible material 40 is provided therein. Compressible material 40 follows the general contour of stem 20 and is adequate in thickness such that when the prosthesis 10 is implanted, persistent proper contact is maintained between the shoulder 37 of collar 36 and the calcar bone C.

Making particular reference to FIG. 1, it is seen that the side of stem 20 opposite ball 32 is straight along its entire length, while likewise making reference to FIG. 2, it is seen that the lateral sides of stem 20 are straight along their entire lengths. The inferior side of stem 20, however, deviates from a straight configuration only as necessary to extend angularly outwardly from a major axis thereof for proper support of ball section 30, which extensions defines buttress section 22. This particular stem configuration of a generally straight, smooth surfaced prosthesis stem is provided to minimize "wedging" of the prosthesis once implanted within the femur. Furthermore, compressible material 40, while ensuring proper contact with the calcar, also due to its compressible nature assists in minimizing wedging of prosthesis 10.

As shown in the Figures, stem 20 of prosthesis 10 is devoid of any holes, fenestrations, indentations or the like, and presents a smooth outer surface. In fact, stem 20 is preferably polished to a mirror finish. When implanted in the femur F, stem 120 is surrounded by luting agent L such as bone cement (See FIG. 6). With the outer surfaces around stem 120 smooth and straight, and preferably highly polished, a minimum of shear stress is transmitted from the prosthesis across the prosthesis-luting agent interface I. The danger of cracking of the luting agent is thus minimized, leading to prolonged implanted life of the prosthesis.

Additionally as is illustrated in FIGS. 1, 2 and 5, a compressible material 45 is preferably received about the distal tip 27 of the prosthesis 10, such that a minimum of axial compressive stress is transmitted from the distal tip 27 of the prosthesis to the luting agent surrounding same when implanted or to the femur, per se. While the compressible material 45, 245 is illustrated in FIGS. 1, 2 and 5, FIG. 6 illustrates a further embodiment of a means for avoiding such transmission of axial compressive stress. In FIG. 6, a receiving element or sleeve 150 is provided about the distal tip 127 of the prosthesis stem 120 and defines an elongated opening 152 therewithin, into which distal tip 127 resides. Receiving element 150 is secured within the femoral cavity and itself is surrounded by an appropriate luting agent L. The cross section of opening 152 within receiving element 150 closely approximates the cross section of the distal tip 127 of stem 120 such that a light frictional engagement therebetween is realized. In such fashion, luting agent L is precluded from entering receiving chamber 152 around stem tip 127. With the arrangement as illustrated in FIG. 6, should the calcar bone resorb, abrade or deteriorate adequate that prosthesis subsidence is permitted axially within the femur, distal tip 127 will simply move further within receiving chamber 152 without transmitting the adverse axial compressive stresses to the luting agent and thus to the femur, whereby again, prolonged implant life is achieved.

Chamber 152 may contain a closed cell compressible material such as polyurethane foam or one of the biocompatible resilient material set forth hereinafter or which will absorb axial force which precluding the ingress of body fluids therein.

FIG. 5 illustrates a further embodiment of a prosthesis generally 210 according to the present invention which is constructed quite similarly to the prosthesis as illustrated in FIGS. 1-4, with the exception that the ball 232 of ball section 230 is smaller than as depicted in FIGS. 1 and 2. The prosthesis illustrated in FIG. 5 is thus intended for use in conjunction with an acetabular cup (not shown) that will also be implanted during a total hip arthroplasty.

A prosthesis according to the present invention is suitable for surgical replacement of the head alone or as part of a total hip replacement. Once implanted, the prosthesis enables a preponderance of the load carried by the hip to be transferred directly to the calcar region of the femur as axial compressive stresses in a stress distribution that closely simulates the stress distribution in a normal, healthy femur. Resorption of the calcar bone and consequential prosthesis loosening are thus retarded and luting agent stress are reduced. Particularly, the head or ball section of the prosthesis may be of any particular size and shape that is intended for use in hemiarthroplasty surgery or in total hip replacement surgery, with the ball section attached to the neck at any angle or degree of inclination consistent with anatomical limitations and surgical requirements. In like fashion, the neck may be offset or inclined at any angle to the axis of the prosthesis stem consistent with anatomical limitations and surgical requirements. The collar portion of the ball section is juxtaposed to the buttress section of the stem and is inclined to the axis of the stem in order that it may firmly contact the medial cortical margin of the neck osteotomy surface when the stem is inserted in the reamed intermedullary cavity. The collar is the principal structural element of the prosthesis of the present invention, and accordingly should be of adequate thickness so that it can safely support the applied loads throughout the service life of the implant. Fairing of the collar into the neck of the ball section should be limited only by the range of motion needed for the joint and by the requirements of joint stability.

The prosthesis, per se, may be fabricated from any suitable material that exhibits adequate strength and biocompatibility for the purpose of the implant. The high technology metals that are conventional in the manufacture of prostheses are preferred, and as mentioned above, the stem of the prosthesis should not contain holes, fenestrations, grooves or other irregularities that could serve to transfer shear load to the luting agent or to the appositional bone that may develop at any point below the collar-calcar contact. Additionally, all surfaces of the stem should preferably have a mirror polish to minimize load transfer across the prosthesis-luting agent or prosthesis-bone interfaces. Suitable materials for the prosthesis include stainless steel alloys, cobalt-chromium alloys, titanium alloys, and the like, aluminum oxide, ceramics, carbon, polyacetal, polysulfone and other high strength polymers, especially those reinforced with a strong second phase such as graphite fibers.

The compressible material 40 located along a portion of the inferior surface of the buttress section of the stem and the distal tip of the stem may be manufactured of a suitable resilient, biocompatible material as exemplified by silastic rubbers, polyurethane rubbers, polyethylenes, polypropylenes and the like. Such likewise could be reinforced with fibers or polymer particles. Such could also contain fully enclosed pores that were filled with air or other highly compressible gas to increase the bulk compressability of the material. These pores would be completely embedded within the solid material and would not communicate with the surface. Compressible materials 40 may be attached to the prosthesis in any desired fashion, such as mechanical fixation by interdigitation of the compressible material with suitable grooves, notches, protrusions or the like in the prosthesis surface or by direct chemical bonding with a suitable adhesive.

The following Examples validate the thesis of the improved prosthesis according to the present invention and demonstrate the relative improved effectiveness of same.

EXAMPLE 1

In order to evaluate the prosthesis design according to the present invention, five pairs of adult human femurs were excised from imbalmed cadavers. All specimens were determined free of gross lesions and anatomical abnormality by visual inspection and x-ray. One femur from each pair was cleaned and a rosette type, electrical resistance strain gage was cemented to the medial surface of the calcar femorale. Additionally uniaxial strain gages were cemented to each bone on the lateral surface just below the greater trochanter, on the medial surface below the level of the lesser trochanter, on the medial surface above the level where the prosthesis tip would reside, and on the medial surface distal to where the tip would reside.

Each selected femur, with instrumentation attached, was secured at its distal end in a holding jig, and was placed in a mechanical testing machine. Compressive loads were applied in 50 pound increments up to 450 pounds to the head of the femur along a line passing through the center of the head and the center of the distal condyles. Each bone was exposed to the loading regime six times. Strains were noted at each gage location and readings used to calculate principal strains for the calcar location. Particularly maximum axial (compressive) strains and maximum hoop (tensile) strains were determined which are a function of applied load. Results are tabulated in Table I.

EXAMPLE 2

Each of the five femurs from Example 1 was appropriately drilled and a standard commercial Austrian Moore femoral component (F.C.) prosthesis was implanted therein with bone cement following standard surgical procedure. Each specimen was then retested according to the procedures set forth in Example 1, the gage readings recorded, and the strains calculated therefrom. Results are tabulated in Table I.

EXAMPLE 3

The five femurs of Example 2 (with prosthesis implanted) were modified by cutting a 3 mm slot in the cement and bone along the line of contact between the prosthesis collar and the osteotomy. All collar-calcar contact was thus effectively removed, simulating improper prosthesis implantation or conditions following resorption of calcar bone. The slot dimension of 3 mm was based on clinical observations that a majority of cases of subsidence of prostheses involve movement of 3 to 5 mm, and that movement of greater than 4 mm may be associated with chronic deep infection. After undermining the collar, the loading tests of Example 1 were repeated with calculated strains being tabulated in Table I.

EXAMPLE 4

The Moore prosthesis employed in Example 2 was modified to generate simulated prostheses generally according to the teachings of the present invention. While it was not possible to exactly duplicate a prosthesis according to the present invention, the Moore prosthesis was modified as follows:

(1) A tapered or relieved area was machined on the medial surface of the stem buttress, and the relieved area filled in with RTV silastic rubber. (See element 40 of FIG. 1).

(2) The anterior, posterior, lateral and medial surfaces of the stem below the collar were machined to remove taper in the stem Grooves in the anterior and posterior surfaces were filled in with silver solder and machined smooth. All surfaces were then polished whereby the stem was rendered smooth and untapered throughout its length. The resulting cross sectional area of the stem was smaller than would occur with a commercial prosthesis incorporating the instant design.

(3) An RTV silicon rubber tip was attached to the distal end of the prosthesis similar to that shown in FIG. 5.

The opposite femur of each pair from which the femurs of Example 1 were chosen were then tested in the same manner as set forth in Examples 1, 2 and 3. In other words the opposite femurs were:

(a) instrumented and tested in tact;
(b) implanted with a modified prosthesis and tested; and
(c) a 3 mm slot was cut beneath the prosthesis collar to undermine same, and the femur was tested. All strain results are tabulated in Table I.

TABLE I

| | | Principal Strains in the Surface of the Femoral Calcar | | | | | | | | |
|---|---|---|---|---|---|---|---|---|---|---|
| | | AUSTIN-MOORE PROSTHESIS | | | | CLEMSON PROSTHESIS | | | | |
| Femur, | Case | Pcomp | % Decrease | Ptens | θ* | R/L | Pmin | % Decrease | Max | θ |
| 2736 L | Intact | −771 | | 67 | 2.7 | R | −1237 | | 100 | −1.6 |
| | Prosthesis | −390 | 49 | 165 | 6.6 | | −656 | 47 | 174 | −22.1 |
| | Undermined | −37 | 95 | 251 | −6.6 | | −460 | 63 | 227 | −30.2 |
| 2787 R | Intact | −874 | | 178 | −8.8 | L | −1580 | | 127 | 12.6 |
| | Prosthesis | −154 | 82 | 271 | 17.4 | | −583 | 63 | 22 | 27.9 |
| | Undermined | −161 | 82 | 364 | 23.1 | | **−573 | 68 | 447 | −39.2 |
| 2790 R | Intact | −1078 | | 282 | −2.5 | L | −1486 | | −13 | 10.4 |
| | Prosthesis | −522 | 52 | 137 | 3.0 | | **−229 | 84 | 282 | 17.1 |
| | Undermined | −93 | 91 | 47 | −32.0 | | −15 | 99 | 181 | 15.3 |
| 2795 L | Intact | −1306 | | 185 | 4.4 | R | −2875• | | 347 | −5.3 |

TABLE I-continued

Principal Strains in the Surface of the Femoral Calcar

| | | AUSTIN-MOORE PROSTHESIS | | | | CLEMSON PROSTHESIS | | | |
|---|---|---|---|---|---|---|---|---|---|
| Femur | Case | Pcomp | % Decrease | Ptens | θ* | R/L | Pmin | % Decrease | Max | θ |
| | Prosthesis | −186 | 86 | 238 | −10.4 | | **−2173 | 24 | 29 | −10.4 |
| | Undermined | −10 | 99 | 281 | −18.7 | | −669 | 77 | −14 | −13.3 |
| 2811 R | Intact | −895 | | 326 | −3.9 | L | −2495 | | 419 | 0.4 |
| | Prosthesis | −194 | 78 | 59 | 16.6 | | **−2194 | 14 | 576 | 10.9 |
| | Undermined | −58 | 94 | 54 | 28.6 | | −340 | 86 | 379 | 26.3 |

*Angle θ is the estimated angle of deviation.
**Stem lubricated with silicone to ensure no shear load across stem-cement interface.

As can be seen from the results set forth in Table I, a significant decrease in compressive strain is experienced in the femur when the Moore prosthesis is implanted therein. Such of course refers to the shielding of the calcar as noted hereinabove. Moreover, when the collar of the Moore prosthesis is undermined, virtually no compressive strain remains (−10 to −161). Conversely, with three out of four of the modified prostheses according to the present design (2790L excluded), significantly less percentage reduction in compressive strain on the femur was experienced. Such indicates that the prosthesis of the present invention more closely approximates the strain experienced by the normal femur, even when the collar is undermined to simulate subsistence of the prosthesis.

Having described the present invention in detail, it is obvious that one skilled in the art will be able to make variations and modifications thereto without departing from the scope of the invention. Accordingly, the scope of the present invention should be determined only by the claims appended hereto.

That which is claimed is:

1. An improved hip prosthesis for implantation for improved axial compressive loading of the calcar while avoiding wedging and axial load transfer from the distal tip of the prosthesis stem to the femur comprising:
   (a) a medullary stem which includes a buttress section, a middle section and a distal tip section, all being of unitary construction, having smooth outer surfaces and being devoid of any irregularities therealong; and
   (b) a head secured to said stem, said head including a ball for articulation within an acetabulum, a neck section distal to said ball and a collar section located between said neck section and said buttress section of same stem and defining a shoulder on an under side of same, said head being angularly offset from said stem according to anatomical criteria for proper contact between said shoulder of said collar section and an osteotomized calcar bone surface, said buttress section having a relieved inferior surface from a point adjacent to said collar downwards to said middle section with compressible material located therein extending along said inferior surface and being adequate in thickness to ensure persistent contact between the collar and the calcar bone and reduce wedging of the prosthesis within the femur, and said stem having a uniform cross section from said middle section distally to a tip of said distal tip section, whereby when implanted with a luting agent around at least a portion of said stem, said collar will maintain contact with the calcar bone for transmittal of axial compressive stresses thereto while said smooth stem surface precludes transmission of any significant shear forces on said luting agent adjacent thereto.

2. An improved hip prosthesis for implantation for improved axial compressive loading of the calcar while avoiding wedging and axial load transfer from the distal tip of the prosthesis stem to the femur comprising:
   (a) a medullary stem, said stem including a buttress section, a middle section, and a distal tip section, all of unitary construction; and
   (b) a head of unitary construction with said stem, said head including a ball for articulation within an acetabulum, a neck section distal to said ball and a collar section juxtaposed between said neck section and said buttress section of said stem, said buttress section having a relieved inferior surface from a point adjacent to said collar downwards to said middle section with compressible material located therein and said compressible material being adequate in thickness to ensure persistent contact between said collar and the calcar bone, the remainder of said buttress section and said middle and distal tip sections of said stem having straight sides therealong to said distal tip, said sides having smooth surfaces and being devoid of irregularities to minimize wedging within the femur and to minimize the transmission of shear forces to a luting agent around said stem.

3. A prosthesis as defined in claim 1 wherein said stem and head are of unitary structure.

4. A prosthesis as defined in claim 1 wherein said distal tip is provided with a compressible material whereby should an axial force be produced on said prosthesis, significant amounts of same will not be transmitted distal to said tip of said stem.

5. A prosthesis as defined in claim 1 comprising further a receiving element received about at least a portion of said distal tip of said stem for relative movement therebetween and extending below same, said element being implantable in the medullary cavity along with said prosthesis, whereby upon receipt of adequate axial force on said prosthesis, said distal tip will move further into said sleeve while avoiding transfer of axial compressive forces to said portions of said medullary cavity thereabout.

6. A prosthesis as defined in claim 2 wherein said tip section has a compressible material received thereabout, whereby upon receipt of axial forces on said prosthesis after implantation, significant axial force distal to said tip is precluded.

7. A prosthesis as defined in claim 2 wherein said stem has a low friction coating therealong.

* * * * *